United States Patent
Serrero et al.

(10) Patent No.: US 10,953,139 B2
(45) Date of Patent: *Mar. 23, 2021

(54) ELECTRO-SPUN CARDIOVASCULAR IMPLANT

(71) Applicant: Xeltis, AG, Zurich (CH)

(72) Inventors: Aurelie Serrero, 's-Hertogenbosch (NL); Martijn Antonius Johannes Cox, Budel (NL)

(73) Assignee: Xeltis AG, Zurich (CH)

( * ) Notice: Subject to any disclaimer, the term of this patent is extended or adjusted under 35 U.S.C. 154(b) by 171 days.

This patent is subject to a terminal disclaimer.

(21) Appl. No.: 16/225,045

(22) Filed: Dec. 19, 2018

(65) Prior Publication Data

US 2019/0201588 A1 Jul. 4, 2019

Related U.S. Application Data

(60) Provisional application No. 62/611,431, filed on Dec. 28, 2017.

(51) Int. Cl.
| | | |
|---|---|---|
| *A61L 27/58* | (2006.01) | |
| *A61L 27/50* | (2006.01) | |
| *A61L 27/14* | (2006.01) | |
| *A61F 2/24* | (2006.01) | |
| *A61L 27/54* | (2006.01) | |

(Continued)

(52) U.S. Cl.
CPC .......... *A61L 27/58* (2013.01); *A61F 2/2415* (2013.01); *A61L 27/14* (2013.01); *A61L 27/50* (2013.01); *A61L 27/507* (2013.01); *A61L 27/54* (2013.01); *A61F 2/06* (2013.01); *A61L 2430/20* (2013.01); *D01D 5/0015* (2013.01)

(58) Field of Classification Search
CPC .......... A61L 27/58; A61L 27/14; A61L 27/50; A61L 27/507; A61L 27/56; A61L 31/04; A61L 31/041; A61L 2430/20; A61L 2430/22; A61F 2/06; A61F 2210/0004; A61F 2250/0059

See application file for complete search history.

(56) References Cited

U.S. PATENT DOCUMENTS 10,766,995 B2 * 9/2020 Coury ................ C08G 18/6674
10,876,222 B2 * 12/2020 Edouard Naz ....... D01D 5/0046

(Continued)

FOREIGN PATENT DOCUMENTS

| WO | WO2005042641 A1 | 5/2005 |
| WO | WO2014185779 A1 | 11/2014 |

(Continued)

OTHER PUBLICATIONS

Drossner et al. A management strategy for mild valvar pulmonary stenosis. Pediatr Cardiol. May 29, 2008(3):649-52 doi: 10.1007/s00246-007-9191-y.

*Primary Examiner* — Paul B Prebilic
(74) *Attorney, Agent, or Firm* — Lumen Patent Firm

(57) ABSTRACT

A biodegradable cardiovascular implant is provided for growing cardiovascular tissue in a patient. The implant distinguishes an electro-spun network with supramolecular compounds having hard-blocks covalently bonded with soft-blocks resulting in much enhanced durability and fatigue resistance, while maintaining the effectiveness as a cardiovascular implant.

1 Claim, 3 Drawing Sheets

(51) Int. Cl.
*A61F 2/06* (2013.01)
*D01D 5/00* (2006.01)

(56) References Cited

U.S. PATENT DOCUMENTS

| | | | |
|---|---|---|---|
| 2009/0130172 A1* | 5/2009 | Dankers | C08G 18/4833 |
| | | | 424/426 |
| 2010/0280594 A1 | 11/2010 | Sahatjian | |
| 2015/0173921 A1 | 6/2015 | Lavrijsen | |
| 2016/0115272 A1* | 4/2016 | Mes | C08G 18/12 |
| | | | 528/73 |
| 2018/0015202 A1* | 1/2018 | Dankers | C08G 71/02 |
| 2018/0274131 A1* | 9/2018 | Naz | D01D 5/0046 |
| 2018/0325646 A1* | 11/2018 | Burke | A61L 33/007 |

FOREIGN PATENT DOCUMENTS

| | | | | |
|---|---|---|---|---|
| WO | WO-2016120456 A1 * | 8/2016 | | A61L 27/26 |
| WO | WO2016120456 A1 | 8/2016 | | |
| WO | WO-2019129640 A1 * | 7/2019 | | D01F 6/78 |

\* cited by examiner

ELECTRO-SPUN CARDIOVASCULAR IMPLANT

CROSS-REFERENCE TO RELATED APPLICATIONS

This application claims priority from U.S. Provisional Patent Application 62/611,431 filed Dec. 28, 2017, which is incorporated herein by reference.

FIELD OF THE INVENTION

This invention relates to electro-spun cardiovascular implants.

BACKGROUND OF THE INVENTION

Current cardiovascular substitutes and implants encounter risks due to coagulation, infections, degeneration, and no growth possibilities. Tissue engineering is a fairly new approach which uses patient's own cells and a biodegradable polymer scaffold to make autologous tissue that is able to grow, adapt and repair. Polymeric scaffolds can be constructed from biocompatible, non-toxic polymers. The choice of polymer and the technique used to make the scaffold effects the mechanical properties exhibited by the scaffold.

For cardiac tissue engineering, the most commonly used biodegradable synthetic scaffold materials are polyglycolic acid (PGA), polylactic acid (PLA), polyhydroxybutyrates (PHB), ε-polycaprolactone (PCL) or their copolymers. US20150173921 teaches the use of supramolecular compounds as the basis of the biodegradable synthetic scaffold for cardiovascular implants.

Despite the recent advances, there is still an unmet medical need, in particular, since cardiovascular substitutes and implants such as heart valves, and hereby preferably for aortic or pulmonary heart valves, have to pass high standards as provided by the FDA and the relevant guidelines such as ISO 5840-1:2015, ISO 5840-2:2015 and ISO 5840-3:2015. An important emphasis for said high standards is hereby placed on hydrodynamic, durability, and, in particular, on fatigue testing to ensure reasonable assurance of safety, effectiveness and FDA approval.

The present invention addresses this unmet need by providing tissue engineered cardiovascular implant with enhanced durability and fatigue resistance, while maintaining the effectiveness as a cardiovascular implant.

SUMMARY OF THE INVENTION

A biodegradable cardiovascular implant is provided for growing cardiovascular tissue in a patient, comprising an electro-spun network having {in alternate embodiments described as 'consisting essentially of' or 'consisting of'} supramolecular compounds having hard-blocks covalently bonded with soft-blocks, wherein the soft-blocks are a polycarbonate soft-blocks each with a molecular weight range of 500-2000, and wherein the hard-blocks comprise 2-ureido-4[1H]-pyrimidinone (UPy) compounds and chain extenders at a range of 1.5 to 3 for the chain extenders over the UPy compounds.

Embodiments of the invention show much enhanced durability and fatigue resistance, while maintaining the effectiveness as a cardiovascular implant.

DETAILED DESCRIPTION

Figure 1:
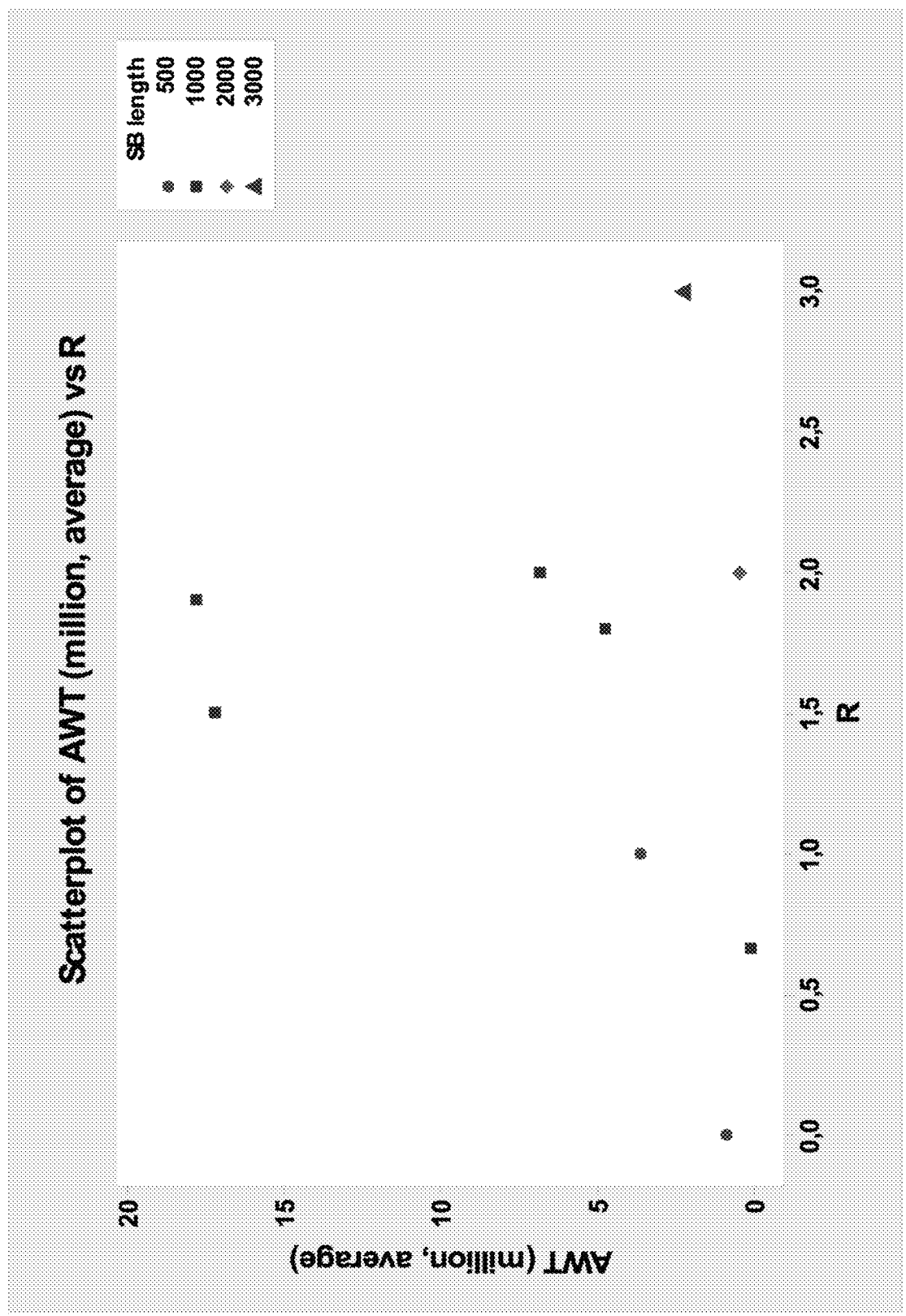
FIG. 1 shows according to embodiments of the invention a number of accelerated wear cycles (according to ISO 5840, aortic conditions) versus R ratio. It is clear that polymers with a polycarbonate of 1000 g/mol and an R ratio of 1.5 and above exhibit enhanced durability. In addition, the same polymers with ratio of 1.5, 1.9 and 2 used in other valve designs exhibited AWT counts up to 65, 123 and 78 million cycles respectively.

The present invention provides tissue engineered cardiovascular implant with enhanced durability and fatigue resistance, while maintaining the effectiveness as a cardiovascular implant.

Supramolecular compounds are defined as hard-blocks covalently bonded with soft-blocks. The hard blocks are based on UPy moieties. The soft block is the backbone of the supramolecular compounds. Polycarbonate (PC) was used as it showed surprisingly benefit for the purposes and objectives of this invention, especially compared to polycaprolactone.

The ratio between the soft block and the hard block has an influence on the material properties. Herein, we describe that ratios of components within the hard block section has a tremendous impact on properties such as durability. We disclose here a specific combination of ratios within the hard block and length of the polymer used to form soft block that lead to enhanced mechanical properties (durability). Specifically, polycarbonate with a molecular weight range of 500-2000 provide enhanced durability and reduced fatigue compared to e.g. polycaprolactone. The hard block is composed of the Upy component, a diisocyanate and a chain extender. The ratio (R) within the hard-blocks for 2-ureido-4[1H]-pyrimidinone (UPy) compounds and chain extenders at a range of 1.5 to 3 for the chain extenders over the UPy compounds.

Example 1: Synthesis of Supramolecular Polymers

PCL Polymer—XP1, XP2

To synthetize XP1, telechelic hydroxy terminated polycaprolactone with a molecular weight of 800 g/mol (30.0 g, 37.5 mmol, dried under vacuum), 1,6-hexanediol (4.4 g, 37 mmol), and UPy-monomer (6.3 g, 37 mmol) were dissolved in dry DMSO (105 mL) at 80° C. To this reaction mixture was added hexamethylene diisocyanate (18.8 g, 111.5 mmol) while stirring, followed by the addition of one drop of tin dioctoate. This reaction mixture was stirred overnight at 80° C. The next day, the reaction mixture was cooled to 25° C. and its viscosity was lowered by the addition of additional DMSO in order to precipitate the mixture in water. The polymer was collected as white elastic solid, redissolved in chloroform/methanol (7/3 v/v) and reprecipitated in an excess methanol. This resulted in a clear elastic solid after drying under vacuum at 50° C. SEC (THF, PS–standards): Mn=13 kg/mol, Đ=1.6. See also WO2014185779A1. XP2 is synthesized in a similar manner, with the exception of the quantity of 1,6-hexanediol which is increased to 74 mmol. The composition of XP1 and XP2 polymers are summarized in TABLE 1.

PC Polymer—XP3

Polymers made with polycarbonates with molecular weight varying from 500 to 3000 g/mol were synthetized in a similar manner as for XP1. The changes were made depending on the length of the polycarbonate and the desired ratio between the components. Molar ratio can be expressed as followed. A (polycarbonate) is fixed at 1. B (chain extender) varies between 0 and 3, D (Upy) from 0.3 to 2 and and C is always equal to 0.8 to 1.2 times the total molar amount of A plus B plus D. Molar ratio B/D is noted R. For the purpose of this invention, XP3 was synthesized by using a polycarbonate molecular weight of 2000 g/mol and selecting a molar ratio R of 2. The composition of XP3 is summarized in TABLE 1.

If not otherwise mentioned, the thickness in the examples is 500 μm for all polymers.

Example 2: Fatigue Testing—Comparison of PC and PCL Based Heart Valves

Description of the Test

The accelerated wear test is a test aimed at evaluating durability of devices. The device is subjected to pressure conditions simulating in vivo conditions and the number of cycles before failure is recorded. Details about durability assessment are described in ISO 5840-3:2013.

First the PVs are tested for 20 min at 30/10 mmHg (20 mmHg) to check opening of the leaflets: maximum/mean systolic pressure gradient, effective orifice area and regurgitation. This pressure condition is classified as a normotensive pulmonary condition (ISO 5840-3:2013). At the start, and after 20 min data and high-speed movies are acquired. The maximum systolic pressure gradient should be below 25 mmHg (Drossner et al. Pediatr Cardiol. 2008 May; 29(3):649-52 doi: 10.1007/s00246-007-9191-y.), and the effective orifice area should be larger than 30% of the geometric orifice area.

Subsequently the valve is tested for 20 hours at 90/35 mmHg, which is classified as very severe hypertensive pulmonary conditions (ISO 5840-3:2013). At the start, after 20 minutes, and after 20 hours (or after failure) data and high-speed movies are acquired.

The materials tested are summarized in TABLE 1 and results are shown in TABLE 2. We observe that the PC-based polymer provides better results after 20 hours compared to PCL based polymers. XP3 shows the best fatigue resistance in the series tested, with no observed tears.

TABLE 1

List of materials

| Material | Soft block | Ratio R |
|----------|------------|---------|
| XP1 | PCL 800 | 1 |
| XP2 | PCL 800 | 2 |
| XP3 | PC 2000 | 2 |

TABLE 2

Valve testing results after 20 hours at 90/35 mmHg

Figure 3C:
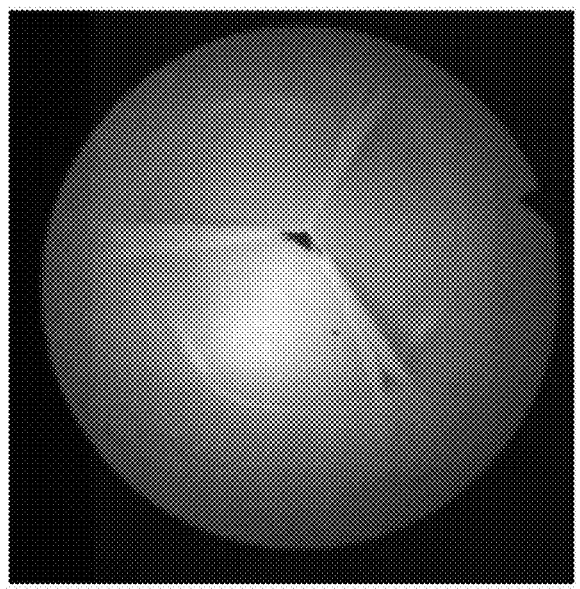
FIGS. 3A-C show according to embodiments of the invention and in relation to Table 2 images of valve testing results after 20 hours at 90/35 mmHg. It is clear that XP3 remains intact whereas XP1 and XP2 show tears.
Figure 3B:
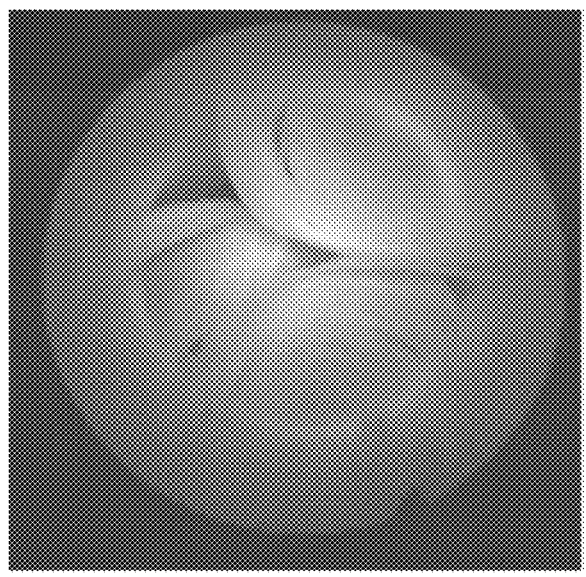
Figure 3A:
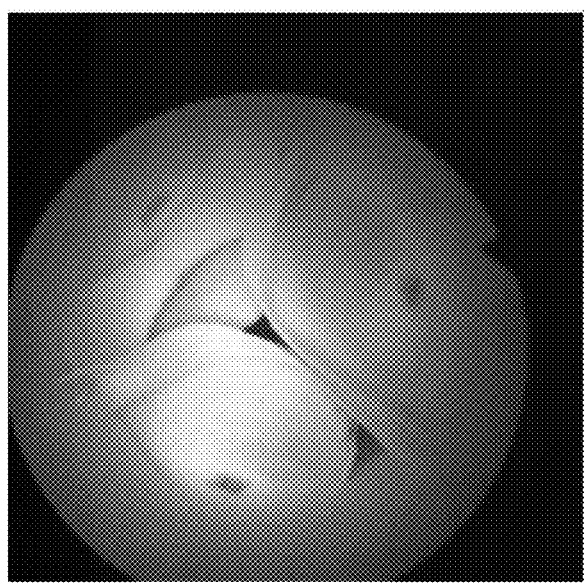

| Material | Outcome (After 20 hr at 90/35 mmHg) | Image (After 20 hr at 90/35 mmHg) |
|----------|-------------------------------------|-----------------------------------|
| XP1 | Tears | FIG. 3A |
| XP2 | Tears | FIG. 3B |
| XP3 | Intact | FIG. 3C |

Pulmonary valve electrospun with PCL polyol (described in PCL/synthesis) as the leaflet material were tested in a valve tester. The pulmonary-valved conduit are evaluated after 20 hours at 90/35 mmHg (very severe hypertensive pulmonary conditions according to ISO 5840-3:2013). Leaflet made with PCL polyol showed tears and failure. On the contrary, leaflets made with PC polyol showed good results (TABLE 2).

The enhanced fatigue resistance of PC based polymers was further tested in aortic conditions (120/80 mmHg). The polymers were dissolved and further electro-spun and assembled to a stent to form an aortic valve. The valves were further tested in aortic conditions at 10 Hz. Within the PC based polymer family, it was then possible to discriminate which polymers gave the best results. FIG. 1 shows the influence of the ratio R on the fatigue resistance. The ration was varied from 0 to 3. The soft block length was varied from 500 to 3000 g/mol. It is observed that polymers with R values of 1.5 and above provides the best fatigue behavior. In addition, there is an unexpected optimum in fatigue resistance when the soft block length is 1000 g/mol.

Figure 2:
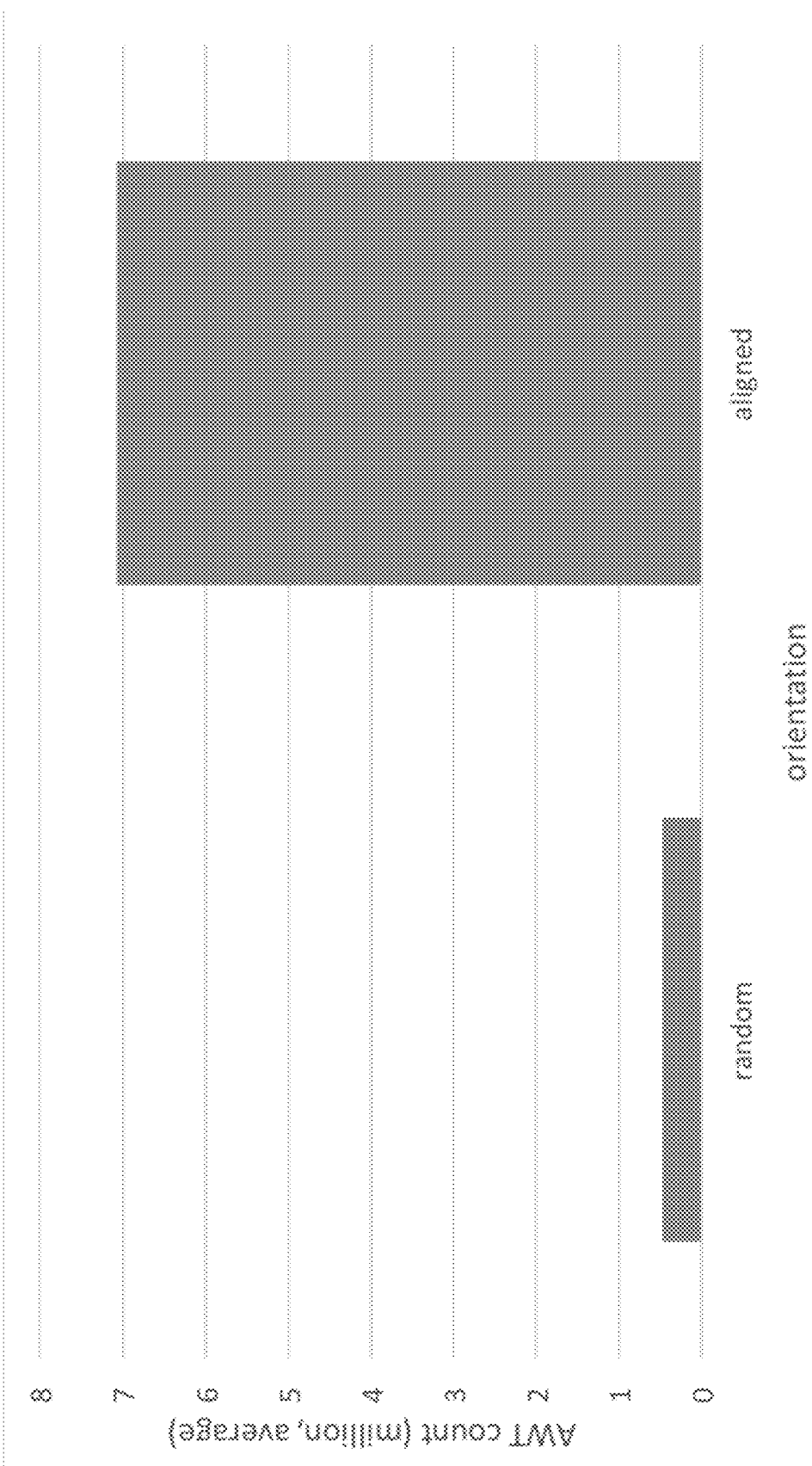
FIG. 2 shows according to embodiments of the invention a number of accelerated wear cycles (according to ISO 5840, aortic conditions) versus orientation of the fibers. It is observed that higher cycle counts can be obtained with aligned fiber compared to random fibers.

An additional feature that can also influence durability is the alignment of the fibers within the scaffold. The preferred fiber alignment is circumferential around an imaginary axis of the implant wherein the axis points in the direction of blood flow in case of a tubular implant. We can clearly see that alignment enables the increase in fatigue resistance from FIG. 2. Alignment, defined as the linear elastic stiffness ratio between the preferred fiber direction and perpendicular to the preferred fiber direction was varied up to 8:1.

Complementary Information

1. Ranges (Durability Focus)

The ratio R was varied from 0 to 3. Enhanced/best fatigue resistance behavior was obtained for ratio of 1.5 and above.

PC length was varied from 500 to 3000 g/mol. Enhanced/best fatigue resistance behavior was obtained for PC length of 1000.

Chain extender mass ratio was varied from 0 to 15. Enhanced/best fatigue resistance behavior was obtained for higher ratio (9 wt % and above).

2. Scaffold Structure

Thickness can be varied between from a few μm to mm, but preferred thickness is between 200 and 800 μm and even preferable between 250 and 550 (average at 300 and 500 provide good results).

Fiber diameters can be obtained in a big range from 1 μm to 20 μm. Preferably, we work in 3-15 μm range and even more preferably in the 4-10 μm range.

Alignment of fibers is another parameter that enhances durability especially when the electrospinning is not guided resulting in a random distribution to a 1:2 (Circumferential: Axial) organization (meaning stiffness in the axial direction is twice the one in the circumferential direction). The fibers can be aligned with a ratio from infinity:1 to 1:2. It is preferable to work with a ratio between 2:1 to 8:1 as they provide good improvement in durability.

Pore size: the matrix material comprises pores having a diameter ranging from 1-300 micrometer and preferably ranging from 5-100 micrometer.

Porosity: the matrix material comprises a fibrous network and has a porosity of at least 60%, preferably a porosity of between 70% and 85%.

What is claimed is:

1. A biodegradable cardiovascular implant for growing cardiovascular tissue in a patient, comprising an electrospun network having supramolecular compounds having hard-blocks covalently bonded with soft-blocks, wherein the soft-blocks are polycarbonate soft-blocks each with a molecular weight range of 500-2000, and wherein the hard-blocks comprise 2-ureido-4[1H]-pyrimidinone (UPy) compounds and chain extenders at a range of 1.5 to 3 for the chain extenders over the UPy compounds.

* * * * *